United States Patent [19]

Kaiser

[11] Patent Number: 5,287,520
[45] Date of Patent: Feb. 15, 1994

[54] MONITOR SYSTEM HAVING LIST OF ITEMS WITH FIXED TIME SLICES FOR TRANSMITTING TIMING SIGNALS AT THE END OF A COMMUNICATION BETWEEN MASTER PROCESSOR AND SLAVE PROCESSORS

[75] Inventor: Winfried Kaiser, Nufringen, Fed. Rep. of Germany

[73] Assignee: Hewlett-Packard Company, Palo Alto, Calif.

[21] Appl. No.: 389,000

[22] Filed: Aug. 3, 1989

[30] Foreign Application Priority Data

Aug. 6, 1988 [EP] European Pat. Off. ........ 88112861.5

[51] Int. Cl.⁵ .......................... G06F 1/04; G06F 13/00
[52] U.S. Cl. .................................. 395/725; 340/825.5; 340/825.06; 364/229; 364/270.1; 364/270.3; 364/DIG. 1; 364/931.44; 364/934; 364/934.1; 364/DIG. 2
[58] Field of Search ........... 395/800, 550, 700, 825.06, 395/725; 370/46, 50, 120; 328/56, 58, 59, 63; 377/20, 114, 115; 340/172.5, 309.15, 309.4, 309.3, 825.06, 825.08, 825.65, 825.5

[56] References Cited

U.S. PATENT DOCUMENTS

| | | | |
|---|---|---|---|
| 3,587,054 | 6/1971 | Byrne et al. | 340/172.5 |
| 3,596,256 | 7/1971 | Alpert et al. | 340/172.5 |
| 3,702,989 | 11/1972 | Provenzano, Jr. et al. | 340/172.5 |
| 3,812,472 | 5/1974 | Mahood | 395/550 |
| 3,925,762 | 12/1975 | Heitlinger et al. | 340/150 |
| 3,969,703 | 7/1976 | Kwaitkowski et al. | 340/172.5 |
| 4,030,073 | 6/1977 | Armstrong, Jr. | 395/775 |
| 4,052,929 | 10/1977 | Deutsch et al. | 84/1.24 |
| 4,280,138 | 7/1981 | Stock | 358/150 |
| 4,335,426 | 6/1982 | Maxwell et al. | 395/725 |
| 4,379,294 | 4/1983 | Sutherland et al. | 340/825.5 |
| 4,688,172 | 8/1987 | Wright | 395/700 |
| 4,728,959 | 3/1988 | Maloney et al. | 342/457 |
| 4,744,218 | 5/1988 | Edwards et al. | 340/825.06 |
| 4,747,332 | 5/1988 | Uchiyama et al. | 84/1.23 |
| 4,780,885 | 10/1988 | Paul et al. | 375/40 |
| 4,809,267 | 2/1989 | Higuchi et al. | 340/825.06 |
| 4,811,561 | 3/1989 | Edwards et al. | 340/825.06 |
| 4,839,890 | 6/1989 | Semerau et al. | 370/84 |
| 4,882,730 | 11/1989 | Shinmyo | 340/825.08 |
| 4,916,692 | 4/1990 | Clarke et al. | 370/85.1 |
| 4,942,573 | 7/1990 | Woodward | 370/85.9 |
| 5,012,411 | 4/1991 | Policastro et al. | 364/413.06 |
| 5,095,425 | 3/1992 | Hesse | 395/550 |

FOREIGN PATENT DOCUMENTS 0210365 2/1987 European Pat. Off. .
2003276A 3/1979 United Kingdom .

*Primary Examiner*—Thomas C. Lee
*Assistant Examiner*—Meng-Ai T. An

[57] ABSTRACT

A system for measuring a plurality of parameters comprises a master processor and a multiplicity of slave processors. The master processor operates in time slices of 2 ms. Communication with the slave processors is performed in fixed format. The master processor manages the communications in certain time slices according to a matrix wherein each item or column represents a certain time slice. The items or columns in this matrix are organized such that the communications with those slave processors preceding the communication with a specific slave processor are the same as in all other items or columns containing a communication with said specific slave processor. In particular, the slave processors requiring short-intervallic timing signals are entered on top of the items or columns, whereas slave processors with longer-intervallic timing signals are entered below these.

This system and the method of communication are particularly useful in a configurable medical monitoring system.

12 Claims, 6 Drawing Sheets

MONITOR SYSTEM HAVING LIST OF ITEMS WITH FIXED TIME SLICES FOR TRANSMITTING TIMING SIGNALS AT THE END OF A COMMUNICATION BETWEEN MASTER PROCESSOR AND SLAVE PROCESSORS

This invention relates to a monitor system and a method for exchanging data between a master processor and a multiplicity of slave processors.

BACKGROUND OF THE INVENTION

The present invention will be described in detail in association with a configurable medical monitoring system. It is to be understood, however, that the invention is not limited to any such system.

Modern medical monitors are of the configurable type, i.e. they comprise a host system and parameter modules. The host system usually includes a cabinet containing the host processor, the operating system, a power supply and so on; a display; a keyboard and a plug-in cabinet or rack for the insertion of parameter modules. Further components like a printer or a plotter may also be included. The parameter modules contain the front end electronics required to measure a specific medical parameter such as ECG (electrocardiogram), respiration, blood pressure, temperature, blood gases and so on. For example, if we consider the ECG, the associated parameter module contains the electronics required for lead selection, a preamplifier and, if data transmission to the host system is performed in digital format, an analog-to-digital conversion circuit. Each of the parameter modules contains the front end electronics for at least one medical parameter of interest; but it is also possible to combine frequently used parameters (such as ECG and respiration) in a single parameter module.

The parameter modules have a connector jack for the insertion of an electrode connector, e.g. a connector which is connected with the ECG electrodes via a cable. The parameter modules include means which permit their insertion into a cabinet or a rack of the host system. This provides full flexibility in choosing only those parameters for monitoring which are required for a specific patient. In other words, the system can be "adapted" to specific clinical requirements, e.g. in the operating room, the recovery room, the intensive care unit or for a special kind of disease.

To provide electrical isolation, the parameter modules are usually connected with the host system via optical couplers.

The parameter modules further need clock or timing signals for the purpose of data acquisition. In order to obtain meaningful results, data acquisition has to be performed in equidistant intervals. Therefore, each parameter module has to be supplied with timing signals at fixed intervals which are used as start signals of an analog-to-digital conversion cycle.

Unfortunately, the intervals between said timing signals are not identical for all parameters, i.e., different parameter modules may require different sampling periods. For example, the ECG has to be sampled every 2 ms (milliseconds) in order to obtain a smooth and meaningful ECG waveform, while temperature need only be sampled every 32 ms.

To meet these timing requirements it would be possible to provide each parameter module with an internal timer which would generate the timing signals necessary for the data acquisition of said module. This, however, has the disadvantage of requiring a plurality of timers, which increases the cost and size of the system. Further, communication between the parameter modules and the host system is rather difficult in this case as this communication can only be performed on an asynchronous basis. Such asynchronous communications may generate several problems. For example, if every parameter module which has converted a sample of data into digital format is programmed to send an inquiry or interrupt to the host system in order to transmit its data, it may occur that certain inquiries overlap in time. If we assume, however, that data transmission from the parameter modules to the host system is only performed after an inquiry from the host system, the number of data samples which a certain parameter module has converted into digital format since the last inquiry is not necessarily constant. Therefore, the length of the communication between the host system and a certain parameter module may vary which further increases the difficulties in such a so-called "handshake" based system. Also, in such a system the parameter modules each need their own memory space for buffering of converted data samples.

The difficulties arising from asynchronous communication can be overcome by using a synchronous data transmission format, i.e. communication in fixed time intervals or slices and with a predefined number of bytes to be transmitted. With synchronous communication, however, internal timers cannot be used; timing signals must be provided either by a central clock or the host system. For the transmission of such timing signals, additional wiring and at least one additional optical coupler for every parameter module has to be provided. Due to the high cost of optical couplers and additional wiring, this solution is not feasible. Further, to avoid transmitting separate timing signals to the parameter modules, which require timing signals of differing intervals, the timing signal transmitted from the host system must be further individually divided or modified by the parameter modules to generate their appropriate timing signals. A solution to overcome this disadvantage is to use the end of a synchronous communication as a timing signal, i.e. a "start of conversion" signal. This is only possible, however, if not more than one parameter module is addressed during a certain time slice of the synchronous transmission. If more than one parameter module is addressed in each time slice and if the modules are not identical (which is necessarily the case in a multiparameter system with different analog to digital conversion cycles) the periods of the timing signals are not equal due to the varying length of the transmission times of the various parameters.

SUMMARY OF THE INVENTION

It is an object of this invention to provide an efficient method and apparatus for communication between a master processor and a plurality of slave processors.

In accordance with this invention, a method is provided for exchanging data between a master processor and a multiplicity of slave processors. The method comprises providing a list of items associated with fixed time slices. Each item of the list defines a set of communications with certain ones of the slave processors during a time slice and each successive item of the list is associated with successive time slices. The method includes effecting communications between the master processor and slave processors in accordance With each successive item in the list until the list is exhausted and, preferably, in rotating order.

In accordance with this invention, a monitor system comprises a master processor and a plurality of parameter modules. The master processor is coupled with the parameter modules by at least a bidirectional Communication channel. Each of the parameter modules includes a slave processor and an analog-to-digital converter. The slave processors control the analog-to-digital converters. The master processor is programmed for exchanging communications with the slave processors in accordance with a list of items associated with fixed time slices and for effecting communications between the master processor and the slave processors in accordance with each successive item in the list in rotating order.

In further accordance with this invention, the slave processors of the modules are programmed to respond to an inquiry of the master processor with a communication and utilize the end of the communication as a timing signal.

In the preferred embodiment of the invention, any item in this list defines a set of communications with certain slave processors. For example, item No. 1 may contain communications with an ECG module, a blood pressure module and a temperature module. During the associated time slice, the master processor communicates with these slave processors in the same order as they are contained in the item. The next time interval is processed in similar manner in that the master processor communicates with the slave processors contained in the next item, and so on, until the list is exhausted. When all of the items are processed, the master processor starts again with item No. 1 of the list. As used herein and in the claims, this is referred to as "rotating order". The items are arranged such that the communications with the slave processors, entered into an item before a communication with a specific slave processor, are always the same in all items containing communications with this specific slave processor. For example, if an item contains the following set of communications with slave processors (ranked in descending order): ECG, blood pressure, pleth, then all other items also containing pleth must have the same rank order of communications as ECG, blood pressure, pleth, regardless of any following communication (which indeed may be different). That is, an item containing ECG, blood pressure, pleth, temperature is not in conflict with another item containing ECG, blood pressure, pleth and CO (cardiac output) Further, an item containing ECG, blood pressure and SaO2 (oxygen saturation) is also allowed, but no item containing ECG, blood pressure, SaO2 and pleth. In the latter case, the parameters (slave processors) preceding pleth are not identical to the first example; therefore, this item is not allowed. In the discussed examples, the several slave processors are, for the purpose of explanation, associated with medical parameters. It is to be understood, however, that the present invention is also suited for other systems with comparable requirements.

The method and the system according to the invention provide a combination of several advantages. In particular, the feature of a very compact and time-saving data transmission format is combined with the feature that necessary timing signals may be transmitted using the normal communication between the master processor and the slave processors. Therefore, the timing signals need not be transmitted via additional lines and optical couplers. Further, there is the capability of transmitting timing signals at different intervals to slave processors which require different sampling periods. The periodicity of these timing signals is ensured by the structure of the items which are used for communication during certain time slices or intervals by the master processor. Preferably, modules of the monitor system or the slave processors use the end of the communication with the master processor as the timing signal, e.g. for the start of an analog-to-digital conversion.

Transmission of a timing signal with a period longer than the duration of time interval may be easily performed by entering the communication with the associated slave processor only in selected, but not in all items of the list. For example, if we use time intervals with a duration of 2 ms (milliseconds) and want to transmit a timing signal with a period of 4 ms to a specific slave processor, a communication with this slave processor has to be entered into every second item of the list.

The communication with a specific slave processor may be performed in several ways. For example, it may be addressed directly by addressing means. It is also possible to connect all slave processors with a common bus and to send an addressing byte to a certain slave processor to initiate communication with it. During the communication, data bytes may be exchanged as well as control information or status information.

Advantageously, the list of items is organized in matrix-like structure, the columns each containing a set of communications with slave processors, whereby the master processor performs the communications with the slave processors in a time slice in the same order as contained in the associated column. That is, the items form the columns of the matrix, each column containing a set of communications, whereas the individual communications form the rows of this matrix. A matrix organized in this fashion simplifies the use of the list by the master processor.

It may be explained here that a specific problem arises if the individual slave processors are addressable, but the type of slave processor at a certain address is originally unknown. This may be the case in a medical monitoring system as described above with several slots in a cabinet or rack wherein the system has originally no information on the position of the parameter modules which were inserted into the various slots. In such a system, the parameter modules must first be identified. A method of dealing with this problem in accordance with the present invention is, for example, to have the master processor transmit an identifying inquiry to all slots in the cabinet or rack with the slave processors responding with an identifying code when their slot is addressed. The master processor then has to generate a list as described above. In accordance with an important preferred embodiment of the invention, this is effected by entering communication with slave processors requiring short sampling periods on top of the columns of the matrix (or items of the list), whereas slave processors requiring longer sampling periods are entered below these, and so on. By applying this simple rule, it can be ensured that a list is generated which meets the requirement of generating timing signals for each parameter module at fixed intervals. Also, if a plurality of slave processors control the analog to digital conversion of sampled parameters requiring equal sampling periods, then communications with the plurality of slave processors are entered in like rank in each column (or items of the list) in which the communications with the plurality of slave processors are entered. The present invention broadly relates to the method for generating such a list as well as to a system programmed to perform this method.

Other features and advantages of the invention will become apparent from the following more detailed description, taken in conjunction with the accompanying drawings, which illustrate, by way of a non-limiting example, the principles of the invention.

DESCRIPTION OF THE PREFERRED EMBODIMENTS

Figure 1:
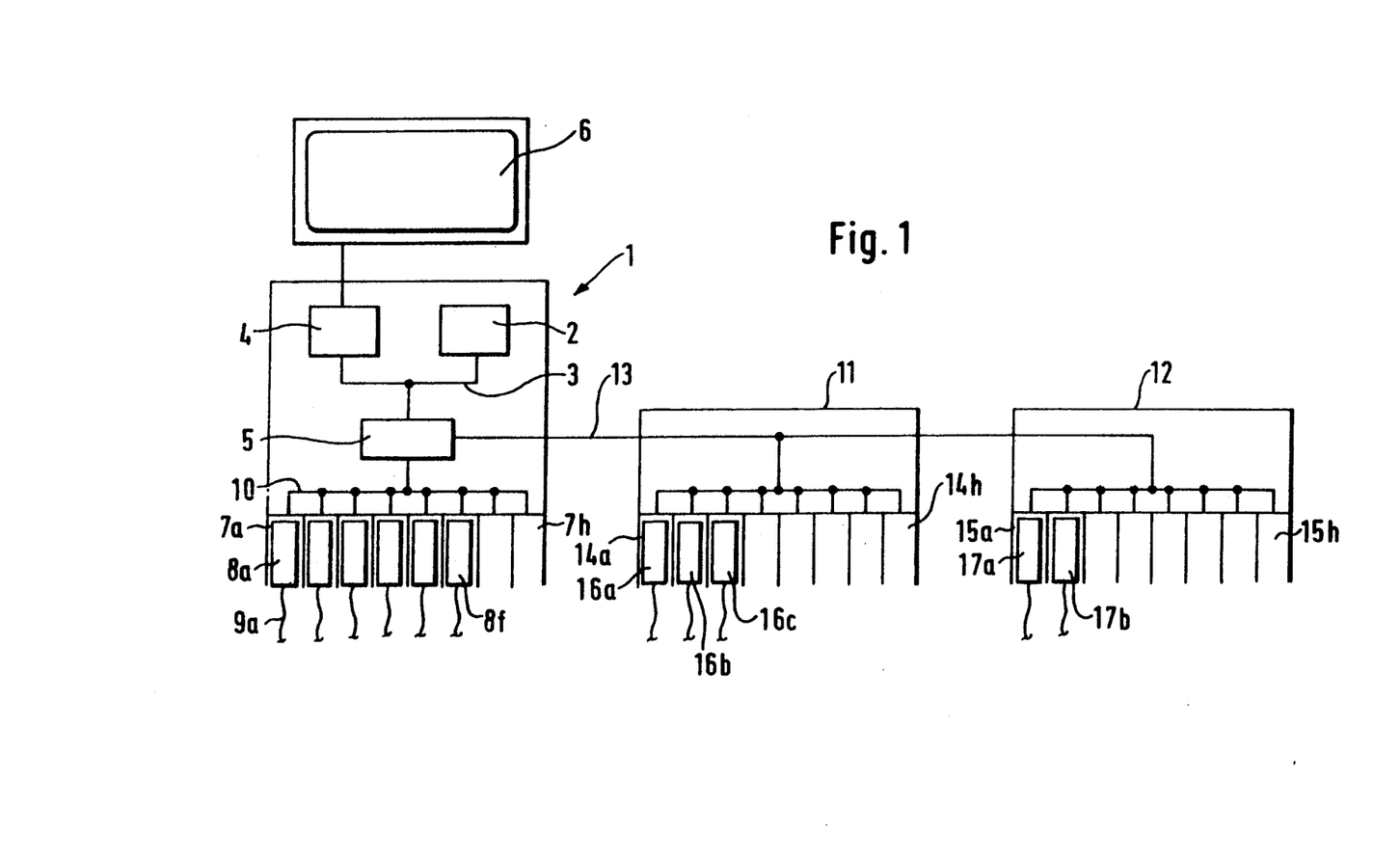
FIG. 1 depicts an overall diagram of a configurable medical monitoring system.

The overall diagram of FIG. 1 depicts a configurable medical monitoring system. A monitor, shown generally at contains a host processor 2. The host processor 2 coordinates the communication with all other parts of the system and executes the operating system program. It is connected via an internal data bus 3 with a display processor 4 and a master processor 5. Display processor 4 controls a display unit 6 which is used to display waveforms and trends of the monitored patient as well as for data entry. Data entry may be performed via a keyboard (not shown) or by other suitable means, such as a touch screen.

Monitor 1 further comprises an internal rack or cabinet with a multiplicity of slots 7a to 7h (for illustration purposes, only slots 7a and 7h are labelled in FIG. 1). These slots are provided for insertion of parameter modules, six of which are shown in FIG. 1 (8a to 8f, wherein only the first and the last module are labelled). Any parameter module contains the front end electronics to measure a certain parameter of medical interest. Parameters of this type are, for example:

ECG (electrocardiogram)
invasive blood pressure,
temperature,
pleth,
non-invasive blood pressure,
blood gases like $pO_2$ or $pCO_2$,
cardiac output,
further blood parameters such as $SaO_2$ (oxygen saturation) or the pH-value of the blood,
the concentration of inspired or expired gases ($O_2$, $CO_2$).

All parameter modules include front end connectors for the insertion of the connector of an electrode cable. For example, parameter module 8a could be an ECG module, and cable 9a could lead to a multiplicity of ECG electrodes. The details of the electrodes or transducers, their cables and the connection of these cables to the parameter modules are not shown in FIG. 1.

When inserted into one of the slots, the parameter module, which includes connector means not shown, is connected with internal data bus 10 and is under the control of master processor 5. This master processor controls the communication with all parameter modules. The front end electronics contained in the parameter modules comprises preamplification, preprocessing (e.g. filtering) and analog-to-digital conversion of the received signals. Further, it comprises electrical isolation between the host system and the electrodes, e.g. by optical couplers. This ensures that the parameter module is not connected with the ground potential of the host system, i.e. it is "floating".

Slots 7a through 7h are identical, even in their connectors to the parameter modules, so that a parameter module may be inserted into any free slot.

The medical monitoring system further comprises two racks 11 and 12. These racks are separated from the monitor and may, e.g. be placed near the patient's bed. These racks are connected via a bus 13 with master processor 5 and are also controlled by this processor. They comprise slots 14a to 14h and 15a to 15h for the insertion of parameter modules. These slots are identical to slots 7a to 7h. Therefore, the parameter modules may be inserted either into slots 7a to 7h of the monitor or into one of the slots of the racks, 11, 12 depending on the application. For example, if the patient has to be monitored in various rooms such as an operating room and a recovery room, it may be desirable to leave the electrodes and transducers connected to the patient in place during transportation. Under these circumstances, a rack such as one of racks 11 or 12 may be attached to the patient's bed; this rack being connected to a monitor in the operation room. When the patient is to be wheeled into the recovery room, the rack is disconnected from the monitor in the operation room; after transportation into the recovery room, the rack is again connected to a second local monitor in this recovery room. The whole system is therefore flexible or adaptable to various needs. Of course, it is also possible to operate the monitor without additional racks or to cascade more than the two racks shown in FIG. 1.

Therefore, it makes no difference whether a parameter module is inserted into one of the "internal" slots 7a to 7h or into one of the slots 14a to 14h or 15a to 15h of racks 11 and 12. In the example shown in FIG. 1, parameter modules 16a to 16c, 17a and 17b have been inserted into the slots of the racks.

Figure 2:
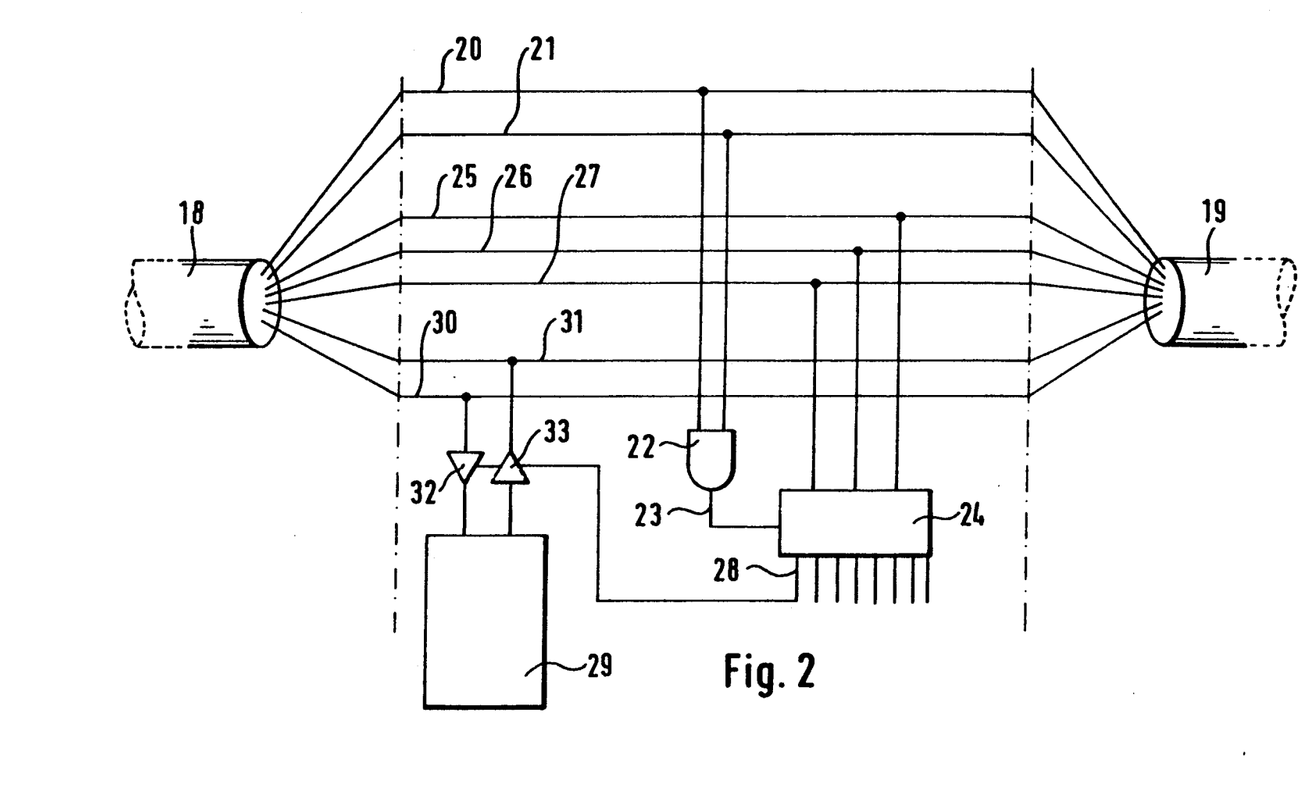
FIG. 2 is a block diagram of the interconnection of a single parameter module.

FIG. 2 depicts a cable 18 for the connection of monitor 1 with a rack. Further racks may be connected via cable 19. The circuit shown in FIG. 2 depicts the details of the addressing and communication means provided for data exchange between master processor 5 and a parameter module. The hardware elements shown there are integrated in a rack. It is understood that this scheme does not only apply to external racks, but also to the internal slots 7a to 7h (although no cables are necessarily required for connection there).

Two address lines 20 and 21 are provided for addressing a specific rack. Therefore, a maximum of four racks may be addressed. The signals on address lines 20 and 21 are fed to an AND-gate 22 which generates a logical "1" at its output (23) if the rack shown in FIG. 2 is addressed. Output 23 is fed to the "enable" input of a decoder 24. This decoder further receives the signals on three address lines 25, 26 and 27 which are used to address a single slot, i.e. a slot within the rack having a single parameter module therein. Decoder 24 generates a "select" signal at output 28 whenever the rack shown in FIG. 2 and a parameter module 29 in this rack are addressed. The other outputs of decoder 24 are used to address other slots/parameter modules (not shown) in the rack.

The "select" signal at output 28 of decoder 24 enables the communication between the master processor and parameter module 29. For this communication, a transmit line 30 and a receive line 31 are provided. These signals are buffered by buffers 32 and 33. Communication may be performed any time parameter module 29 is addressed.

FIG. 2 depicts only the principles of addressing and communication. That is, not all hardware elements, which form no part of the present invention, are contained and described herein. For a more detailed description of these circuits, reference is made to U.S. patent (application Ser. No. 340,981 filed Apr. 20, 1989 and assigned to the assignee of this invention) which is hereby incorporated by reference.

Communication between the master processor and the parameter modules, which contain slave processors, is performed in fixed time slices. For this purpose, the master processor receives an internal clock signal in intervals of 2 ms which causes an interrupt in the master processor. Within such a time slice, the master processor communicates with several parameter modules. An example of such a communication is depicted in FIG. 3a.

Figure 3A:
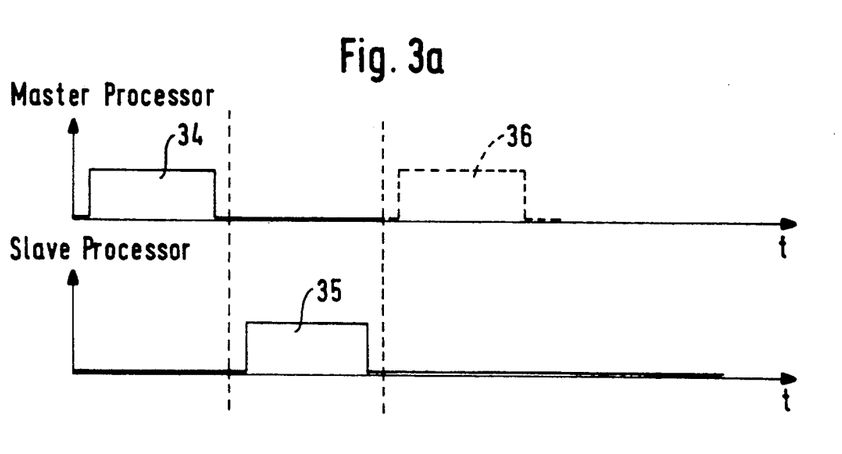
FIGS. 3a and 3b depict timing diagrams of various communications between the master processor in the central monitor and the slave processors in the parameter modules.

Immediately after the interrupt occurs, the master processor (upper diagram in FIG. 3a) addresses a certain slave processor in a parameter module (not shown in FIG. 3a). It then puts a control word (ref. No. 34) on transmit line 30 (FIG. 2). The slave processor responds (ref. No. 35) with a data word on receive line 31 (FIG. 2). This data word is the digital representation of a sample of a medical parameter. Immediately after appliance of data word 35 on receive line 31, the slave processor starts its next analog-to-digital conversion cycle and puts the digitized sample in a buffer for read-out during the next communication. Meanwhile, the master processor addresses the next parameter module as indicated by broken line 36.

The slave processor therefore uses the end of a communication as timing signal for analog-to-digital conversion. If the event "end of communication" occurs in fixed time periods, sampling is also performed in fixed periods. Therefore, no separate transmission of a timing signal is necessary. The problem of triggering a multiplicity of slave processors with fixed periods within one time slice will be discussed below.

Figure 3B:
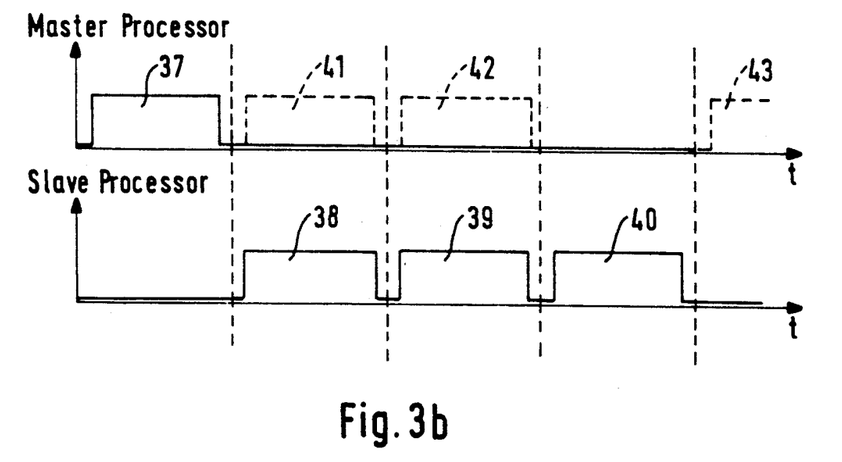

FIG. 3b depicts a further example of a communication between the master processor and a slave processor. Immediately after the interrupt (t=0), the master processor puts the control word on transmit line 30 (ref. No. 37). At the same time, a parameter module is addressed. In the case shown in FIG. 3b, the slave processor in the parameter module responds with the transmission of three data words 38, 39 and 40 on receive line 31. This is an example for a transmission of more than one word. For example, data word 38 may represent a digitized sample, whereas data word 39 contains coded status information of the parameter module, and data word 40 contains further status information. As communication is performed on a bidirectional basis via two separate transmission lines (30 and 31) the master processor may transmit additional control information during receipt of data words 38 to 40. In the shown example, two additional control words transmitted by the master processor are indicated by dashed lines 41 and 42. Addressing of the next parameter module is indicated by dashed line 43 in FIG. 3b.

Figure 4:
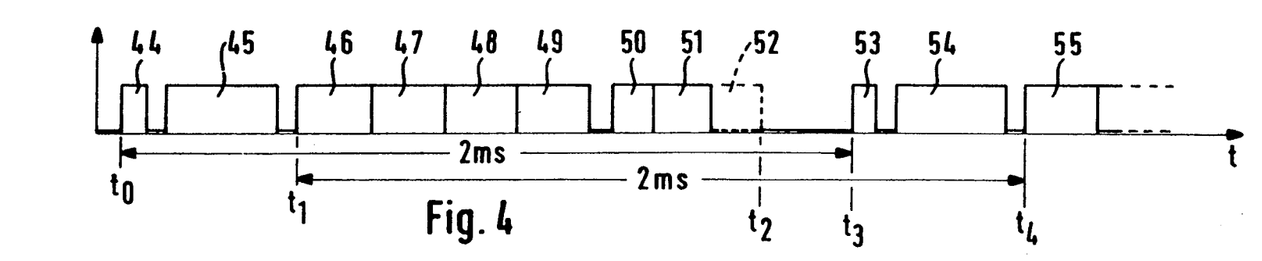
FIG. 4 depicts an internal timing diagram of a single parameter module.

The overall timing diagram of a parameter module is depicted in FIG. 4. At $t=t_0$, the parameter module is addressed, and the master processor puts the control word on transmit line 30 (ref. no. 44). As a response thereto, the parameter module puts a data block 45 on the receive line, this data block comprising one or a few data words containing digitized samples and control information. These words are read out from a buffer, the contents of this buffer having been prepared for transmission prior to the addressing of the parameter module.

As already mentioned, the parameter module uses the end of a communication as a timing signal ($t=t_1$). Upon this event, analog-to-digital conversion is started. In the shown example, the parameter module comprises four data acquisition channels. Block 46 represents the A/D conversion of channel 1, block 47 the A/D conversion of channel 2, block 48 the A/D conversion of channel 3, and block 49 the A/D conversion of channel 4. When the A/D conversion is finished, the slave processor in the parameter module prepares the transmission buffer for the next communication (ref. No. 50), i.e. the digitized samples and status information is written into the transmission buffer. The slave processor then performs other tasks (ref. No. 51), e.g. interpretation of the control information received from the master processor, error handling and so on. In contrast to A/D conversions 46 to 49, these tasks need different time intervals depending on the control information to be processed. This is indicated by dashed line 52.

When these tasks are completed ($t=t_2$), the slave processor waits for the next communication ($t_2 < t < t_3$). At $t=t_3$, the master processor puts the next control word (ref. No. 53) on transmit line 30, and the next cycle starts. Therefore, 54 indicates the next communication and 55 the A/D conversion of channel 1 starting at $t_4$.

A time interval or slice is defined by the period between successive interrupts, and is depicted in FIG. 4 as the interval between $t=t_0$ and $t=t_3$. This time slice corresponds to the interrupt cycle of the master processor. In the shown example, this is an interval of 2 ms.

As the time interval between $t=t_0$ and $t=t_1$, i.e. the time interval for transmitting the control word and performing the communication, is always the same (which implies that $t_1-t_0=t_0=t_4-t_3$) the A/D conversions are also started periodically at 2 ms intervals.

Figure 5:
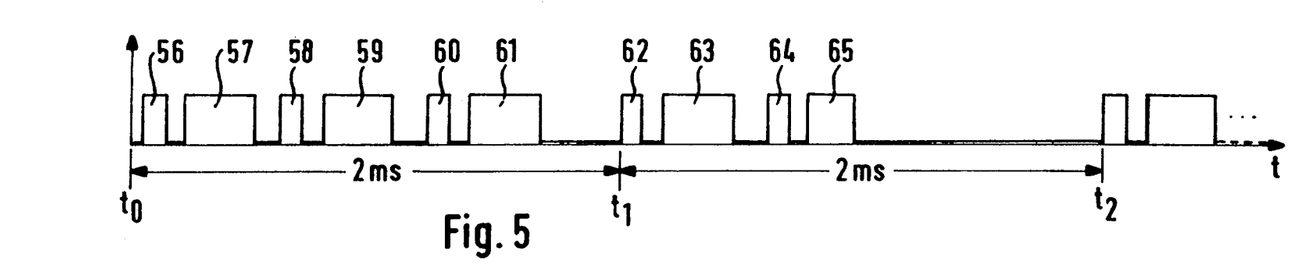
FIG. 5 depicts a timing diagram of the master processor.

FIG. 5 depicts the timing diagram of the master processor. In this diagram, the time slices are defined by the interrupts at $t=0$, $t=t_1$ and $t=t_2$. During the first time slice ($t_0 < t < t_1$), communication with three parameter modules is performed. Ref. No. 56 indicates the transmission of the control word to a first parameter module, and ref. No. 57 the communication with this module. In similar manner, ref. Nos. 58 to 61 indicate the transmission of control words (58, 60) and the communication (59, 61) with two further parameter modules.

During the next time slice ($t_1 < t < t_2$) control word transmission (62, 64) and communication (63, 65) is performed with only two parameter modules. Further communications follow after $t=t_2$.

As will be explained more fully hereinafter with reference to FIGS. 6 and 7, the reason that the communication with the parameter modules may vary from time slice to time slice is simply that not all parameter modules need to perform an A/D conversion every 2 ms. For example, the invasive blood pressure must be sampled every 4 ms and temperature every 32 ms, whereas the ECG has a sampling period of 2 ms. Therefore, communication with the ECG module is performed in every time slice, whereas communication with the invasive blood pressure module is only performed in every second time slice and communication with the temperature module every 16$^{th}$ time slice. For example, in the timing diagram shown in FIG. 5 ref. Nos. 56, 57, 62 and 63 may refer to a communication with the ECG module, ref. Nos. 58 and 59 to a communication with the invasive blood pressure module, ref. Nos. 60 and 61 to a communication with a temperature module and ref. Nos. 64 and 65 to a communication with a pleth module. As all parameter modules need first time intervals or periods between their various timing signals, it must be ensured that these timing signals are generated appropriately. This will now be explained by references to FIG. 6.

Figure 6:
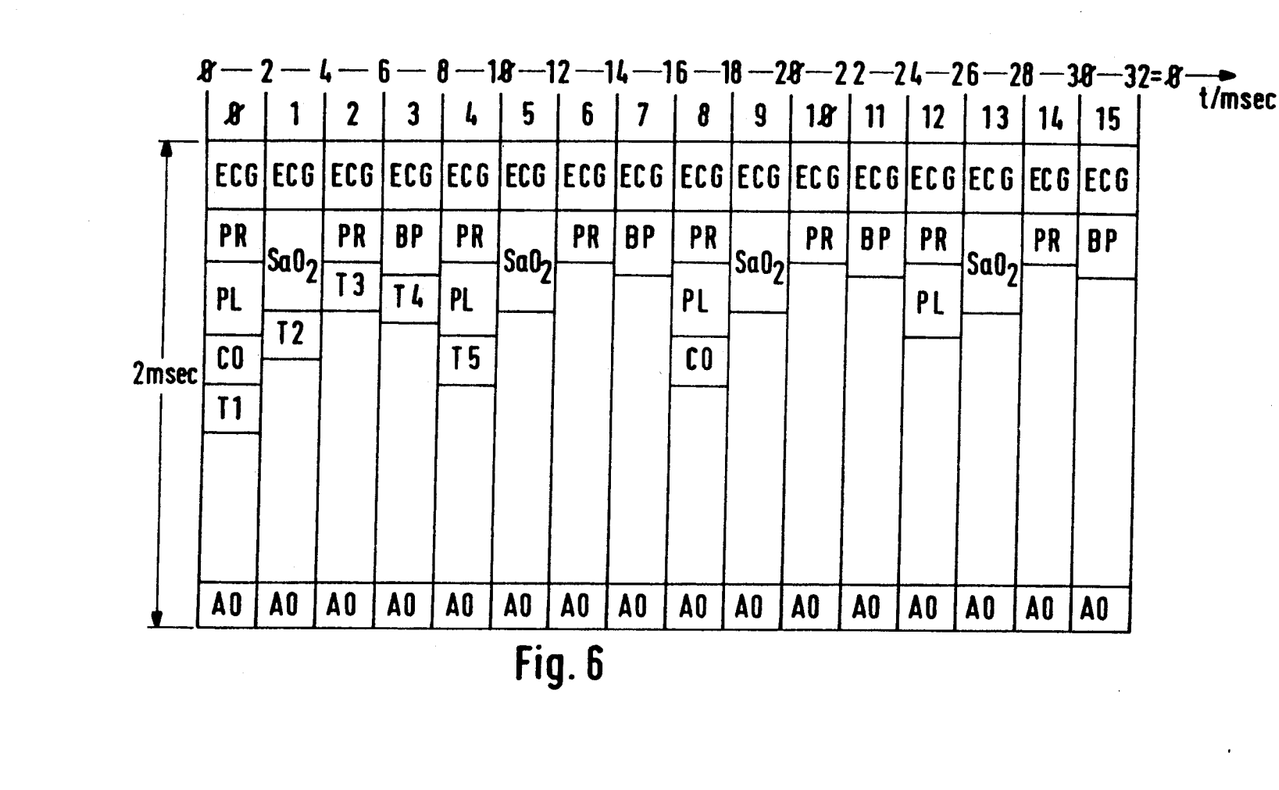
FIG. 6 depicts a list in matrix form defining communications from the master processor to the slave processors and FIG. 7 is another version of this list useful to explain timing considerations.

FIG. 6 depicts a matrix-like structure which is used by the master processor to manage the communication with the slave processors in certain time slices. This matrix comprises sixteen columns numbered from 0 to 15, each column representing the communications during a certain time slice. Any column contains information for communicating with several parameter modules which are subject to addressing and to communication during the associated time slice. Therefore, every column represents a time slice of 2 ms. As indicated in the upper-most line of FIG. 6, the whole matrix therefore represents 16×2 ms=32 ms.

Upon power-on of the monitor, the position of the various parameter modules is unknown, i.e. the master processor does not know where a specific parameter module in the slots of the internal or external racks is positioned and which slots are empty. Therefore, the master processor starts an "identifying cycle" by sending an identifying inquiry to all addresses in the system. The parameter modules are programmed to respond with an identifying code. After receipt of this identifying code, the master processor may use this code to identify a specific parameter module by means of an internal reference table which contains all necessary information about this module, in particular about the intervals between timing signals required by this parameter. Alternatively, it is also possible to transfer the required information about a certain parameter module to the master processor during the identifying cycle. This omits the need for a specific reference table in the master processor.

After receipt of all necessary information about the connected parameter modules, the master processor starts to generate the matrix as depicted in FIG. 6. The parameter module with the shortest sampling period, i.e. with the shortest interval between two subsequent timing signals, is entered on top of the list. In the shown example, this is the ECG parameter with a sampling time of 2 ms. As any column in FIG. 6 depicts a time frame of 2 ms, the ECG is entered into every column.

The next parameter to be represented or entered into the matrix is the invasive blood pressure (label "PR") with a sampling time of 4 ms. It is entered in column 0 below the ECG. As only a 4 ms sampling period is required, "PR" is not entered into column 1. "PR" is then further entered into every second column, i.e. columns 2, 4, 6, 8, 10, 11 and 14.

There are three further parameters with a sampling period of 8 ms. These are pleth ("PL"), oxygen saturation ("SaO$_2$") and non-invasive blood pressure ("BP"). These parameters have to be entered in every forth column starting with any desired column. In the shown example, "PL" starts in column 0, "SaO$_2$" in column 1 and "BP" in column 3. Still other arrangements are possible as long as it is ensured that the total time for communication within a certain column/time slice or item/time slice does not exceed two ms. The master processor can control this as the reference table or the identifying data transmitted during the identifying cycle contains information about the duration of a communication with a certain parameter module. For example, a communication including a transmission of 4 bytes needs 125 $\mu$s (micro seconds). The master processor performs this control calculation ("calculation of data link usage") when generating the matrix.

The next parameter to be entered is the "cardiac output" parameter ("CO") with a sampling period of 16 ms. In the example shown in FIG. 6, this parameter is indicated or entered in every eighth column, i.e., in columns 0 and 8.

In the example being described with reference to FIG. 6, the monitor system further comprises five temperature modules T1 to T5. As these parameters need only a sampling period of 32 ms, they are entered into the matrix only once, for example in columns 0 to 4.

For the generation of a matrix in accordance with the invention, there are two important considerations:
1. parameters with longer sampling periods must be entered below parameters with shorter sampling periods, and
2. the total communication time in one time interval must not exceed 2 ms.

Free times in the matrix may be used to perform further functions, e.g. analog output ("AO"). This communication is used to transmit data to a module or a built-in circuit which generates analog signals. Further free times in the matrix may be used to address free slots. Thus, the system is able to detect a further parameter module which was inserted during system operation (if this happens, the matrix must eventually be re-generated).

It is also possible to use sampling periods of less than 2 ms although the 2 ms timing intervals or slices cannot be shortened. In this case, the parameter module must contain an internal timer triggered by the 2 ms timing signal. The internal timer must then generate timing signals with a shorter period, e.g. 500 $\mu$s. Data transmission is still performed in the 2 ms timing interval or cycle; therefore, a device operating with a sampling period of 500 $\mu$s could transmit 4 digitized samples during any communication.

When the matrix is generated by the master processor, normal operation is started. In this mode, the master processor performs communication during the first 2 ms time slice or interval according to item 0 or column 0 of the matrix, i.e. it addresses the ECG module, the invasive blood pressure module, the pleth module, the cardiac output module and the "temperature 1" module in this order and communicates with them. At the end of this time slice, an analog output signal may be generated. For the purpose of correct communication, the matrix has at least one entry for each parameter module containing the address of that parameter module and the number and type of bytes to be transmitted and received.

In the second time slice or interval, the master processor performs the communication according to item 1 or column 1 of the matrix, during the third time interval communication is performed according to item 2 or column 2, and so on. After the 16$^{th}$ time interval (column 15) the whole cycle is started again with item 0 or column 0, i.e. the matrix is processed in rotating order.

Figure 7:
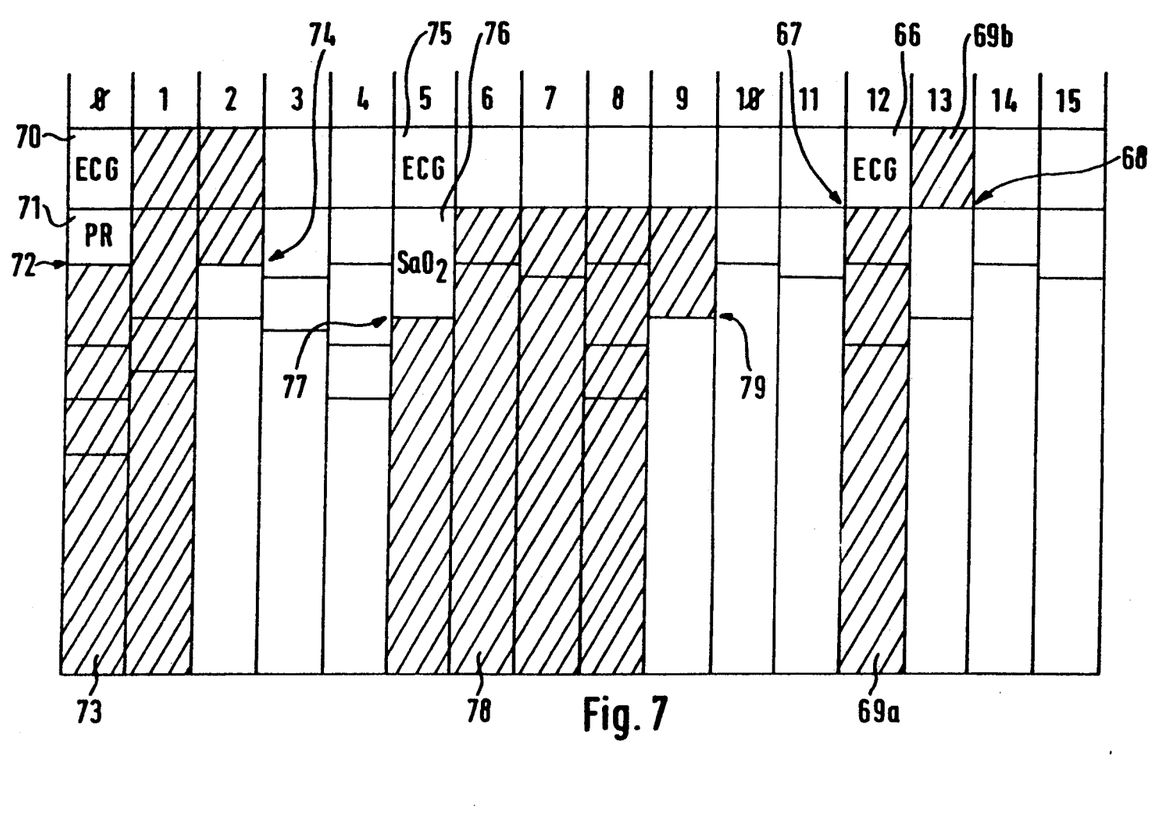

It will now be shown by means of FIG. 7 that the structure of the matrix ensures that all parameter modules receive appropriate timing signals. This Will be shown by means of three parameters with different sampling periods.

The first is the ECG parameter requiring a sampling period of 2 ms. As an example of the internal timing of this parameter, the communication in item 11 or column 11 of the matrix (ref. NO. 66) will be considered. The ECG parameter module uses the end of the communication as a start signal for the analog-to-digital conversion. This is indicated by ref. No. 67. As shown, the time interval until the next A/D conversion occurs (ref. No. 68) is exactly 2 ms (this time interval of 2 ms is indicated by hatched blocks 69a and 69b).

In the next example, the invasive blood pressure module with a sampling period of 4 ms will be considered. A/D conversion (column 0) occurs when the communication with the ECG parameter module (ref. No. 70) and the invasive blood pressure parameter module (ref. No. 71) is completed, start of the A/D conversion is labeled as 72 in this case.

In this example, hatched block 73 indicates the time interval until the next A/D conversion occurs (ref. No. 74). As the parameter preceding the invasive blood pressure in columns 0 and 2 (ECG) uses a fixed format for the communication, i.e. a communication always requires the same time, and as this also applies to the communication of the invasive blood pressure parameter itself, A/D conversion (sampling) is also performed in equal time intervals of 4 ms.

It is evident that this can only be achieved because the parameters preceding the invasive blood pressure are the same in all columns, and because they use a fixed format for communication. If, for example, the parameter preceding the invasive blood pressure would be ECG in one column and SaO$_2$ in another one, equidistant timing intervals could not be guaranteed as SaO$_2$ needs more time for communication with the master processor than the ECG. It can also be readily seen that a matrix fulfilling these requirements can be obtained by entering the parameters with the shortest sampling periods on top of the columns, whereas parameters with longer sampling periods are entered below these. When entering parameters with equal longer sampling periods into the columns of the matrix, they may be entered either in different columns or, alternatively, in the same columns one after the other; in the latter case, attention has to be given to the total communication times in a time interval, i.e. the master processor has to calculate the total length of communications within a time slice and ensure that these communications do not exceed the total time of 2 ms. When generating such a matrix, first the parameters with a sampling period of 2 ms (e.g. ECG) have to be entered, then the parameters with a sampling period of 4 ms (e.g. invasive blood pressure), then the parameters with a sampling period of 8 ms (e.g. SaO$_2$), then the parameters with a sampling period of 16 ms (e.g. CO) and, finally, the parameters with a sampling period of 32 ms (e.g. temperature). Depending on the sampling period, they are entered into every column (sampling period of 2 ms), in every second column (sampling period of 4 ms), every forth column (sampling period of 8 ms), every eighth column (sampling period of 16 ms) or only in one column in the whole matrix (sampling period of 32 ms).

As a last example, the SaO$_2$ parameter with a sampling period of 8 ms will be considered. A/D conversion starts (in column 5) when communication with the ECG parameter module (ref. No. 75) and the SaO$_2$ parameter module (ref. No. 76) has been performed. Start of the A/D conversion is indicated by ref. No. 77. Hatched block 78 indicates the time interval until the next A/D conversion occurs, see ref. No. 79. It can be readily seen that equidistant timing (of 8 ms) is also ensured in this case.

It is understood that the matrix in FIG. 7 is the same as in FIG. 6; merely for the purpose of explanation, several parameters have not been entered with their labels in the matrix of FIG. 7.

It will be appreciated that while particular embodiments of the invention have been shown and described, obviously many modifications and variations of the present invention are possible in the light of the above teachings. It is, therefore, to be understood that within the scope of the appended claims, the invention may be practiced otherwise than as specifically described.

I claim:

1. A method for exchanging data between a master processor and a multiplicity of slave processors of a configurable medical monitoring system, said master processor being able to transmit equidistant timing signals of different intervals to slave processors requiring different sampling periods, wherein each said slave processor has a corresponding communication format and controls an analog to digital conversion of a sampled parameter, said method comprising the steps of:

a) providing a list of items associated with fixed time slices; each item of said list specifying a set of communications with certain ones of said slave processors during a time slice and each successive item of said list being associated with successive time slices, and b) effecting communications between said master processor and slave processors in accordance with each successive item in said list until said list is exhausted, said effecting communications step including transmitting a control word from said master processor to said slave processors, said slave processors using said control word for initiating an analog to digital conversion cycle;

wherein each communication between said master processor and a particular one of said slave processors is in a format that is specified in at least one item in said list and is identical to the format of other communications between the master processor and said particular slave processor; and wherein items of the list provided in step a) are generated by ranking the set of communications with certain ones of said slave processors such that communications with slave processors controlling the analog to digital conversion of a sampled parameter requiring shorter sampling periods are entered ahead of communications with slave processors controlling the analog to digital conversion of a sampled parameter requiring longer sampling periods.

2. A method in accordance with claim 1 further comprising the step of:
repeating step b) in rotating order.

3. A method in accordance with claim 1 further comprising the step of:
prior to step a), determining types of communications to be received from said slave processors.

4. A method in accordance with claim 1 wherein said slave processors control the analog to digital conversion of sampled parameters requiring equal sampling periods and communications with said plurality of slave processors are entered in like rank in each item in which said communications with said plurality of slave processors are entered.

5. A method for exchanging communications between a master processor and a multiplicity of slave processors of a configurable medical monitoring system, said master processor being connected with said slave processors by at least a bidirectional communication channel and each slave processor controlling the analog to digital conversion of a sampled parameter by an analog to digital converter associated with each slave processor; said master processor being able to transmit equidistant timing signals of different intervals to slave processors requiring different sampling periods and each said slave processor has a corresponding communication format, wherein each communication between said master processor and a particular one of said slave processors is in a format that is specified in at least one item in said list and is identical to the format of other communications between the master processor and said particular slave processor, said method comprising the steps of:
a) determining types of communications to be received from said slave processor;
b) based on step a), generating a list of items associated with fixed time slices; each item of said list defining a set of communications with certain ones of said slave processors during a time slice and each successive item of said list being associated with successive time slices, said generating step including ranking said set of communications such that communications with slave processors controlling the analog to digital conversion of a sampled parameter requiring short sampling periods are entered ahead of communications with slave processors controlling the analog to digital conversion of a sampled parameter requiring longer sampling periods, wherein the set of communications in the items of said list are arranged such that the communications with slave processors preceding the communication with a specific slave processor are the same as in all other items containing a communication with said specific slave processor; and
c) effecting communications between said master processor and said slave processors in accordance with each successive item in said list in rotating order.

6. A method in accordance with claim 5 wherein step c) includes the step of transmitting a control word from said master processor to each of said slave processors, each of said slave processors using said control word for initiating an analog to digital conversion cycle by its associated analog to digital converter.

7. A medical monitor system for measuring a plurality of parameters comprising a master processor and a plurality of parameter modules, said master processor being coupled with said parameter modules by at least a bidirectional communication channel, each of said parameter modules including a slave processor and an analog to digital converter, said slave processor controlling the analog to digital conversions of sampled parameters by said analog to digital converters, said master processor being able to transmit equidistant timing signals of different intervals to slave processors requiring different sampling periods, wherein each said slave processor has a corresponding communication format, said master processor being programmed for exchanging communications with said slave processors in accordance with a list of items associated with fixed time slices, and for effecting communications between said master processor and said slave processors in accordance with each successive item in said list in rotating order, wherein said master processor in communication with said slave processors transmit control words over said communication channel, said slave processors using said control words for initiating analog to digital conversion cycles by said analog to digital converters; wherein each item of said list defines a set of communications with certain ones of said slave processors during a time slice and each successive item of said list is associated with successive time slices; wherein each communication between said master processor and a particular one of said slave processors is in a format that is specified in at least one item in said list and is identical to the format of other communications between the master processor and said particular slave processor; and wherein the communications in said items are ranked such that communications with slave processors controlling the analog to digital conversion of a sampled parameter requiring shorter sampling periods are entered ahead of communications with slave processors controlling the analog to digital conversion of a sampled parameter requiring longer sampling periods.

8. A monitor system in accordance with claim 7 wherein said master processor is further programmed to determine the type of communication to be received from each of said slave processors and to generate said list of items.

9. A monitor system in accordance with claim 8 wherein said slave processors control the analog to digital conversion of sampled parameters requiring equal sampling periods, and communications with said slave processors are entered in like rank in each item in which said communications with said plurality of slave processors are entered.

10. A monitor system in accordance with claim 7 wherein each communication between said master processor and a particular slave processor, regardless of which item in the list the communication is contained in, is in a format that is identical to the format of other communications between the master processor and said particular processor.

11. A monitor system in accordance with claim 7 wherein said master processor is further programmed to transmit an identifying inquiry to the slave processors for determining the location of each slave processor in said monitor system and for determining the types of communications to be received from said slave processors.

12. A monitor system in accordance with claim 7 wherein said master processor receives or generates a clock signal for the generation of said time slices.

* * * * *